(12) United States Patent
Rogers et al.

(10) Patent No.: US 8,999,073 B2
(45) Date of Patent: *Apr. 7, 2015

(54) MEDICAL IMPLEMENT CLEANING DEVICE

(71) Applicant: Ivera Medical Corporation, San Diego, CA (US)

(72) Inventors: Bobby E. Rogers, San Diego, CA (US); Paul DiPerna, San Clemente, CA (US)

(73) Assignee: Ivera Medical Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,972

(22) Filed: Sep. 15, 2014

(65) Prior Publication Data

US 2015/0000062 A1 Jan. 1, 2015

Related U.S. Application Data

(63) Continuation of application No. 14/407,458, filed on Dec. 16, 2013, now Pat. No. 8,834,650, which is a continuation of application No. 13/466,976, filed on May 8, 2012, which is a continuation of application (Continued)

(51) Int. Cl.
*A61L 2/18* (2006.01)
*A61M 39/16* (2006.01)
(Continued)

(52) U.S. Cl.
CPC ............... *A61B 19/34* (2013.01); *A61M 39/162* (2013.01); *A61L 2/18* (2013.01)

(58) Field of Classification Search
CPC ....... A61B 19/34; A61M 39/162; A61L 2/18; A61L 2202/24

USPC .................... 15/97.1, 104.92, 104.93, 104.94
See application file for complete search history.

(56) References Cited

U.S. PATENT DOCUMENTS 1,744,026 A 1/1930 Baltzley
1,841,597 A 1/1932 Hammer et al.
(Continued)

FOREIGN PATENT DOCUMENTS

DE 2164821 A1 8/1972
EP 0462355 A1 12/1991
(Continued)

OTHER PUBLICATIONS

U.S. Appl. No. 60/815,806, filed Jun. 22, 2006, Anderson et al.
(Continued)

*Primary Examiner* — Michael Kornakov
*Assistant Examiner* — Natasha Campbell
(74) *Attorney, Agent, or Firm* — Mintz Levin Cohn Ferris Glovsky and Popeo, P.C.

(57) ABSTRACT

A device for cleaning a site of a luer activated valve (LAV) is disclosed. The device can include a cap having an inner cavity for receiving a site of the LAV. The cap can be formed to provide at least one aperture to the inner cavity when the site is received into the inner cavity. The device can also include one or more protrusions that extend inwardly from the cap to engage the site to maintain the cap on the site. The device can also include a cleaning agent that occupies some of the inner cavity. The cleaning agent can be formulated to clean the site as the inner cavity receives the site and when the cap is maintained on the site. The device can further include a removable seal that seals the cleaning agent within the inner cavity prior to the inner cavity of the cap receiving the site.

15 Claims, 7 Drawing Sheets

Related U.S. Application Data

No. 13/189,457, filed on Jul. 22, 2011, now Pat. No. 8,206,514, which is a continuation of application No. 12/860,825, filed on Aug. 20, 2010, now Pat. No. 7,985,302, which is a continuation of application No. 11/705,805, filed on Feb. 12, 2007, now Pat. No. 7,780,794.

(60) Provisional application No. 60/832,437, filed on Jul. 21, 2006, provisional application No. 60/850,438, filed on Oct. 10, 2006.

(51) Int. Cl.
*B08B 3/08* (2006.01)
*A61B 19/00* (2006.01)

(56) References Cited

U.S. PATENT DOCUMENTS

| | | |
|---|---|---|
| 1,937,492 A | 11/1933 | Merolle |
| 2,322,701 A | 6/1943 | Nesset et al. |
| 2,341,285 A | 2/1944 | Petrullo |
| 2,731,963 A | 1/1956 | Blank |
| 2,740,480 A | 4/1956 | Cox et al. |
| 2,993,612 A | 7/1961 | Trautvetter |
| 3,120,879 A | 2/1964 | Warner |
| 3,362,587 A | 1/1968 | Postel et al. |
| 3,391,847 A | 7/1968 | Christine et al. |
| 3,405,831 A | 10/1968 | Hudson et al. |
| 3,431,548 A | 3/1969 | Busier et al. |
| 3,435,978 A | 4/1969 | Wittwer |
| 3,443,686 A | 5/1969 | Raymond et al. |
| 3,651,972 A | 3/1972 | Itoh |
| 3,771,685 A | 11/1973 | Micallef |
| 3,818,627 A | 6/1974 | Lebensfeld |
| 3,979,001 A | 9/1976 | Bogert |
| 3,987,921 A | 10/1976 | Aichinger |
| 3,987,930 A | 10/1976 | Fuson |
| 4,089,463 A | 5/1978 | Babiol |
| 4,169,751 A | 10/1979 | Yen |
| 4,232,677 A | 11/1980 | Leibinsohn |
| 4,257,526 A | 3/1981 | Weits et al. |
| 4,280,632 A | 7/1981 | Yuhara |
| 4,289,248 A | 9/1981 | Lynn |
| 4,335,756 A | 6/1982 | Sharp et al. |
| 4,340,148 A | 7/1982 | Beckham |
| 4,401,227 A | 8/1983 | Pehr |
| 4,432,764 A | 2/1984 | Lopez |
| 4,440,207 A | 4/1984 | Genatempo et al. |
| 4,461,394 A | 7/1984 | Sendel et al. |
| 4,530,726 A | 7/1985 | Montiel |
| 4,564,116 A | 1/1986 | Prohaska |
| 4,572,373 A | 2/1986 | Johansson |
| 4,597,758 A | 7/1986 | Aalto et al. |
| 4,624,664 A | 11/1986 | Peluso et al. |
| 4,655,762 A | 4/1987 | Rogers |
| 4,671,306 A | 6/1987 | Spector |
| 4,674,643 A | 6/1987 | Wilde et al. |
| 4,712,705 A | 12/1987 | Fuehrer |
| 4,752,983 A | 6/1988 | Grieshaber |
| 4,778,447 A | 10/1988 | Velde et al. |
| 4,798,303 A | 1/1989 | Arnold |
| 4,810,241 A | 3/1989 | Rogers |
| 4,991,629 A | 2/1991 | Ernesto et al. |
| 5,065,783 A | 11/1991 | Ogle, II |
| 5,078,693 A | 1/1992 | Shine |
| 5,143,104 A | 9/1992 | Iba et al. |
| 5,169,033 A | 12/1992 | Shay |
| 5,184,742 A | 2/1993 | DeCaprio et al. |
| 5,242,425 A | 9/1993 | White et al. |
| 5,263,606 A | 11/1993 | Dutt et al. |
| 5,277,311 A | 1/1994 | Hollister |
| 5,292,020 A | 3/1994 | Narin |
| 5,385,372 A | 1/1995 | Utterberg |
| 5,385,378 A | 1/1995 | Hakamada et al. |
| 5,398,837 A | 3/1995 | Degrassi |
| 5,409,471 A | 4/1995 | Atkinson et al. |
| 5,445,270 A | 8/1995 | Dratz |
| 5,535,771 A | 7/1996 | Purdy et al. |
| 5,554,135 A | 9/1996 | Menyhay |
| 5,624,402 A | 4/1997 | Imbert |
| 5,694,978 A | 12/1997 | Heilmann et al. |
| 5,702,017 A | 12/1997 | Goncalves |
| 5,743,884 A | 4/1998 | Hasson et al. |
| 5,743,894 A | 4/1998 | Swisher |
| 5,792,120 A | 8/1998 | Menyhay |
| 5,807,345 A | 9/1998 | Grabenkort |
| 5,807,347 A | 9/1998 | Bonaldo |
| 5,947,954 A | 9/1999 | Bonaldo |
| 5,951,519 A | 9/1999 | Utterberg |
| 5,954,957 A | 9/1999 | Chin-Loy et al. |
| 5,989,227 A | 11/1999 | Vetter et al. |
| 6,004,299 A | 12/1999 | Arai et al. |
| 6,027,482 A | 2/2000 | Imbert |
| 6,036,672 A | 3/2000 | Allen et al. |
| 6,045,539 A | 4/2000 | Menyhay |
| 6,102,223 A | 8/2000 | Montgomery |
| 6,116,468 A | 9/2000 | Nilson |
| 6,190,364 B1 | 2/2001 | Imbert |
| 6,196,998 B1 | 3/2001 | Jansen et al. |
| 6,227,391 B1 | 5/2001 | King |
| 6,250,315 B1 | 6/2001 | Ernster |
| 6,293,293 B1 | 9/2001 | Wrigley et al. |
| 6,299,131 B1 | 10/2001 | Ryan |
| 6,364,862 B1 | 4/2002 | Bonilla |
| 6,394,983 B1 | 5/2002 | Mayoral et al. |
| 6,520,935 B1 | 2/2003 | Jansen et al. |
| 6,523,686 B1 | 2/2003 | Bae |
| 6,524,295 B2 | 2/2003 | Daubert et al. |
| 6,527,751 B2 | 3/2003 | Fischer et al. |
| 6,622,882 B2 | 9/2003 | Smith |
| 6,821,267 B2 | 11/2004 | Veillon, Jr. et al. |
| 6,880,801 B2 | 4/2005 | Matkovich et al. |
| 6,911,025 B2 | 6/2005 | Miyahara |
| 6,913,157 B2 | 7/2005 | Oh |
| 7,083,605 B2 | 8/2006 | Miyahara |
| 7,090,191 B2 | 8/2006 | Matkovich et al. |
| 7,118,560 B2 | 10/2006 | Bonaldo |
| 7,188,623 B2 | 3/2007 | Anderson et al. |
| 7,198,611 B2 | 4/2007 | Connell et al. |
| 7,282,186 B2 | 10/2007 | Lake, Jr. et al. |
| 7,316,669 B2 | 1/2008 | Ranalletta |
| 7,329,235 B2 | 2/2008 | Bertron et al. |
| 7,329,249 B2 | 2/2008 | Bonaldo |
| 7,427,275 B2 | 9/2008 | DeRuntz et al. |
| 7,452,349 B2 | 11/2008 | Miyahara |
| 7,500,964 B2 | 3/2009 | Shaw et al. |
| 7,530,977 B2 | 5/2009 | Lodi |
| 7,682,561 B2 | 3/2010 | Davis et al. |
| 7,704,002 B2 | 4/2010 | Fisher et al. |
| 7,780,794 B2 | 8/2010 | Rogers et al. |
| 7,857,793 B2 | 12/2010 | Raulerson et al. |
| 7,922,701 B2 | 4/2011 | Buchman |
| 7,931,618 B2 | 4/2011 | Wyrick |
| 7,931,877 B2 | 4/2011 | Steffens et al. |
| 7,967,779 B2 | 6/2011 | Bertron et al. |
| 7,985,302 B2 | 7/2011 | Rogers et al. |
| 7,988,676 B1 | 8/2011 | Gray |
| 8,061,544 B2 | 11/2011 | Frishman |
| 8,105,293 B2 | 1/2012 | Pickhard |
| 8,162,899 B2 | 4/2012 | Tennican |
| 8,167,847 B2 | 5/2012 | Anderson et al. |
| 8,172,813 B2 | 5/2012 | Janish |
| 8,177,768 B2 | 5/2012 | Leinsing |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,277,422 B2 | 10/2012 | Oliver et al. |
| 8,287,491 B2 | 10/2012 | Burns et al. |
| 8,296,893 B2 | 10/2012 | Vinci et al. |
| 8,303,548 B2 | 11/2012 | Ito et al. |
| 8,641,681 B2 | 2/2014 | Solomon et al. |
| 8,647,326 B2 | 2/2014 | Solomon et al. |
| 8,832,894 B2 | 9/2014 | Rogers et al. |

(56) References Cited

U.S. PATENT DOCUMENTS

| | | |
|---|---|---|
| 8,834,650 B2 | 9/2014 | Rogers et al. |
| 2001/0003150 A1 | 6/2001 | Imbert |
| 2002/0133124 A1 | 9/2002 | Leinsing et al. |
| 2004/0024357 A1 | 2/2004 | Pelkey et al. |
| 2004/0030321 A1 | 2/2004 | Fangrow |
| 2004/0039341 A1 | 2/2004 | Ranalletta |
| 2004/0171993 A1 | 9/2004 | Bonaldo |
| 2004/0172006 A1 | 9/2004 | Bonaldo |
| 2004/0195136 A1 | 10/2004 | Young et al. |
| 2004/0258560 A1 | 12/2004 | Lake et al. |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0214185 A1 | 9/2005 | Castaneda |
| 2006/0030827 A1 | 2/2006 | Raulerson et al. |
| 2006/0048313 A1 | 3/2006 | Yamaki |
| 2006/0189961 A1 | 8/2006 | Miyahara |
| 2006/0253103 A1 | 11/2006 | Utterberg et al. |
| 2007/0106205 A1 | 5/2007 | Connell et al. |
| 2007/0106229 A1 | 5/2007 | Wong |
| 2007/0112333 A1 | 5/2007 | Hoang et al. |
| 2007/0156118 A1 | 7/2007 | Ramsey et al. |
| 2007/0176117 A1 | 8/2007 | Redmond et al. |
| 2008/0019889 A1 | 1/2008 | Rogers et al. |
| 2008/0027399 A1 | 1/2008 | Harding et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0095680 A1 | 4/2008 | Steffens et al. |
| 2008/0128646 A1 | 6/2008 | Clawson |
| 2008/0132880 A1 | 6/2008 | Buchman |
| 2008/0147047 A1 | 6/2008 | Davis et al. |
| 2008/0177250 A1 | 7/2008 | Howlett et al. |
| 2009/0005759 A1 | 1/2009 | Chelak |
| 2009/0008393 A1 | 1/2009 | Howlett et al. |
| 2009/0028750 A1 | 1/2009 | Ryan |
| 2009/0062766 A1 | 3/2009 | Howlett et al. |
| 2009/0099529 A1 | 4/2009 | Anderson et al. |
| 2009/0137969 A1 | 5/2009 | Colantonio et al. |
| 2009/0149819 A1 | 6/2009 | Chelak |
| 2009/0163876 A1 | 6/2009 | Chebator et al. |
| 2009/0205151 A1 | 8/2009 | Fisher et al. |
| 2010/0000040 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0172794 A1 | 7/2010 | Ferlic et al. |
| 2010/0174162 A1 | 7/2010 | Gough et al. |
| 2010/0199448 A1 | 8/2010 | Vazales et al. |
| 2010/0312197 A1 | 12/2010 | Sano et al. |
| 2010/0313366 A1 | 12/2010 | Rogers et al. |
| 2011/0213341 A1 | 9/2011 | Solomon et al. |
| 2011/0265825 A1 | 11/2011 | Rogers et al. |
| 2011/0277788 A1 | 11/2011 | Rogers et al. |
| 2012/0039764 A1 | 2/2012 | Solomon et al. |
| 2013/0019421 A1 | 1/2013 | Rogers et al. |
| 2013/0237911 A1 | 9/2013 | Von Schuckmann |
| 2014/0101876 A1 | 4/2014 | Rogers et al. |
| 2014/0228773 A1 | 8/2014 | Burkholz |

FOREIGN PATENT DOCUMENTS

| | | |
|---|---|---|
| EP | 1061000 A2 | 12/2000 |
| EP | 1977714 A1 | 10/2008 |
| EP | 2135626 A1 | 12/2009 |
| JP | 07-047137 | 2/1995 |
| JP | 07-043674 | 9/1995 |
| JP | 09-206370 A | 8/1997 |
| JP | 09-012829 U | 9/1997 |
| JP | 2001-527441 A | 12/2001 |
| JP | 2002-291906 A | 10/2002 |
| JP | 4234777 B1 | 3/2009 |
| WO | WO-94/11474 A1 | 5/1994 |
| WO | WO-98/48872 A1 | 11/1998 |
| WO | WO-00/24442 A1 | 5/2000 |
| WO | WO-2007/103998 A2 | 9/2007 |
| WO | WO-2007/137056 A2 | 11/2007 |
| WO | WO-2009/136957 A1 | 11/2009 |
| WO | WO-2009/153224 A1 | 12/2009 |
| WO | WO-2011/056221 A1 | 5/2011 |
| WO | WO-2011/120017 A1 | 9/2011 |

OTHER PUBLICATIONS

U.S. Appl. No. 60/832,437, filed Jul. 21, 2006, Rogers.

Byington "Spontaneously Generating Life in Your Classroom? Pasteur, Spallanzani & Science Process," *The American Biology Teacher*, vol. 63, No. 5 (May 2001). pp. 340-345. Published by University of California Press on behalf of National Association of Biology Teachers.

European Patent Office, European Search Report and Opinion for EP Application No. EP 10 78 3956, date of completion of the search Mar. 12, 2014, 7 pgs.

European Patent Office, Supplementary Partial European Search Report and Opinion for EP Application No. 07 75 8117 date of completion of the search Nov. 22, 2012, 6 pgs.

International Search Report and Written Opinion issued in International Application No. PCT/US2008/053744, mailed Jul. 22, 2009.

International Search Report and Written Opinion dated Nov. 9, 2012, PCT/US2012/025517.

International Search Report and Written Opinion issued in International Application No. PCT/US2013/044167, mailed Oct. 16, 2013.

International Search Report and Written Opinion issued in International Application No. PCT/US2014/026716, mailed Jun. 12, 2014.

International Standard ISO 594-2. "Conical Fitting with 6% (Luer) Taper for Syringes, Needles and Certain Other Medical Equipment—Part 2: Lock Fittings". Reference No. ISO 594-2:1998(E), Second edition. (Sep. 1, 1998)1:11.

Japanese Patent Office, Japanese Notice of Reasons for Rejection for Japanese Patent Application No. 2008-558527 dated Apr. 12, 2012.

Japanese Patent Office, Japanese Notice of Reasons for Rejection for Japanese Patent Application No. 2008-558527 dated Apr. 2, 2013.

Material Properties of Polyamide (Nylon), www.madeitfrom.com, pp. 1-2.

Material Properties of Polycarbonate, www.madeitfrom.com, pp. 1-3.

Material Properties of Polypropylene, www.madeitfrom.com, pp. 1-2.

Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of the Society for Healthcare Epidemiology of America*. Infect Control Hosp Epidemiol. vol. 27(2006):23-27.

Menyhay Healthcare Systems LLC available at http://www.menyhaymedical.comimenyhay.html (retrieved Nov. 8, 2013).

The International Bureau of WIPO, PCT International Preliminary Report on Patentability and Written Opinion of the International Searching Authority for International Application No. PCT/US2007/063534 dated Nov. 21, 2007.

Value Plastics Inc, Luer Connectors, http://www.valueplasctics.com/search/search.aspx, pp. 1-2.

MEDICAL IMPLEMENT CLEANING DEVICE

CROSS REFERENCE TO RELATED APPLICATIONS

This application is a continuation of U.S. patent application Ser. No. 14/107,458, filed on Dec. 16, 2013, entitled "Medical Implement Cleaning Device", which is a continuation of U.S. patent application Ser. No. 13/466,976, filed on May 8, 2012, entitled, "Medical Implement Cleaning Device", which is a continuation of U.S. patent application Ser. No. 13/189,457, filed on Jul. 22, 2011, issued on Jun. 26, 2012 as U.S. Pat. No. 8,206,514, and entitled, "Medical Implement Cleaning Device", which is a continuation of U.S. patent application Ser. No. 12/860,825, filed on Aug. 20, 2010, issued on Jul. 26, 2011, as U.S. Pat. No. 7,985,302, and entitled "Medical Implement Cleaning Device", which is a continuation of U.S. patent application Ser. No. 11/705,805, filed on Feb. 12, 2007, issued on Aug. 24, 2010, as U.S. Pat. No. 7,780,794, and entitled "Medical Implement Cleaning Device", which claims the benefit under 35 U.S.C. §119(e) of U.S. Provisional Patent Application Ser. No. 60/832,437, filed on Jul. 21, 2006, and entitled "Disinfecting Cap" and also claims the benefit under 35 U.S.C. §119(e) of U.S. Provisional Patent Application Ser. No. 60/850,438, filed on Oct. 10, 2006, and entitled "Disinfecting Cap". These references are incorporated herein by reference in their entirety for all purposes.

BACKGROUND

Within the medical field, and in particular the area of infusion of fluids or aspiration of fluids to or from a patient, there is a need to prevent the transmission of pathogens into or onto a patient from a potentially contaminated surface of a medical implement, or "site". Such pathogens include microorganisms such as bacteria and viruses. The transmission of pathogens into a patient may result in an infection that could be life threatening. Specific to healthcare settings, the term "nosocomial infection" describes those infections that originate from or occur in a hospital or hospital-like setting. In the U.S., nosocomial infections are estimated to occur in at least 5% of all acute care hospitalizations. The estimated incidence is more than two million cases per year, resulting in an added expenditure in excess of $4.5 billion. Nosocomial infections are estimated to more than double the mortality and morbidity risks of any admitted patient, and likely result in about 90,000 deaths a year in the United States. Common sites for such transmissions are found on such medical implements as a luer port, vial, needle free valve, or an injection port of a vessel, tubing, or catheter. Even non-intrusive medical implements such as stethoscopes can transmit pathogens to a patient. The incidence of infection in patients is presently numerous and increasing, and Infection Control Practitioners (ICP's) often cite improper cleaning of sites as a major source of these infections.

Traditionally, cleaning a potentially contaminated surface includes a protocol of alcohol swabbing prior to making the necessary connections to the site. Today alcohol swabs, a small pad of cotton gauze soaked in isopropyl alcohol, are packed individually in a foil package. The foil package is relatively inexpensive, and is used to retain the alcohol within the package and to prevent evaporation. Properly used, the package is opened at or near the site to be swabbed. With gloved hands, the pad is removed by a healthcare provider and wiped across the top and side surfaces of the site, and the pad and foil package are discarded. The site should be allowed to dry, usually twenty to thirty seconds, immediately prior to making any connection. This "drying" period is important: when alcohol dries, it breaks open the cellular walls of microorganisms, thereby killing them.

Unfortunately, because of increased duties and responsibilities, shrinking nursing staffs, and inadequate training, swabbing is often overlooked or is poorly executed. A poorly swabbed site can carry microorganisms that, if allowed to enter a patient's body, can cause serious infection. In addition, supervisory oversight is nearly impossible, because unless a supervisor can actually observe the swabbing being performed, the supervisor cannot know whether or not it was done properly or performed at all. Further, without at least a sufficient microscopic examination for microbial residue, there may be no evidence of an alcohol swab being performed. Thus, a need exists for an apparatus and technique for cleaning a site on a medical implement prior to contact with a patient, and which will eliminate technique-related issues and training issues, and provide an unequivocal indicator that a site is clean prior to accessing a patient's vascular system.

SUMMARY

A device for cleaning a site for a luer activated valve (LAV) is disclosed. The device includes a cap having an inner cavity for receiving a site of the LAV. The cap is formed to provide at least one aperture to the inner cavity of the cap when the site of the LAV is received into the inner cavity of the cap. The device also includes one or more protrusions that extend inwardly from the cap. The one or more protrusions engage the site of the LAV to maintain the cap on the site of the LAV after the site of the LAV is received into the inner cavity of the cap. The device further includes a cleaning agent that occupies at least some of the inner cavity. The cleaning agent is formulated to clean the site of the LAV as the inner cavity of the cap receives the site of the LAV and when the cap is maintained on the site of the LAV. The device also includes a removable seal that seals the cleaning agent within the inner cavity prior to the inner cavity of the cap receiving the site of the LAV.

The above device can, in some implementations, further include one or more of the following features.

The at least one aperture can allow evacuation of at least some of the cleaning agent from the inner cavity when the inner cavity of the cap receives the site of the LAV.

The one or more protrusions can include threading.

The at least one aperture can be formed between the one or more protrusions that extend inwardly from the cap and the outer surface of the LAV.

The at least one aperture can be provided as the corresponding protrusions on the site of the LAV engage the one or more protrusions that extend inwardly from the cap.

The device can further include a compressible cleaning material in the inner cavity of the cap to contain a portion of the cleaning agent.

In another aspect, a device for cleaning a portion of a luer activated valve (LAV) having an outer surface is disclosed. The device includes a cap for receiving the portion of the LAV. The cap is formed to provide at least one aperture to an inner cavity of the cap when the portion of the LAV is received into the cap. The device also includes one or more protrusions to engage the outer surface of the LAV to maintain the cap on the LAV after the portion of the LAV is received into the cap. The device further includes a cleaning agent within the cap. The cleaning agent is formulated to clean the portion of the LAV as the cap receives the portion of the LAV and as the cap is maintained on the LAV. The device also includes a removable seal that seals the cleaning agent within the cap prior to the cap receiving the portion of the LAV.

The above device can, in some implementations, further include one or more of the following features.

The at least one aperture can allow evacuation of at least some of the cleaning agent from the cap when the cap receives the portion of the LAV.

The one or more protrusions can include threading.

The at least one aperture can be formed between the one or more protrusions of the device and the outer surface of the LAV.

The at least one aperture can be provided as the corresponding protrusions on the portion of the LAV engage the one or more protrusions that extend inwardly from the cap.

In another aspect, a system for cleaning a portion of a luer activated valve (LAV) having an outer surface that includes one or more protrusions is disclosed. The system includes one or more devices. Each of the one or more devices includes a cap having a removable seal that seals a cleaning agent within the cap prior to cleaning the portion of the LAV. The cleaning agent is formulated to clean the portion of the LAV. The cap is formed to provide at least one aperture to an inner cavity of the cap after the removable seal is removed and when the portion of the LAV is received into the cap. Each of the one or more devices also includes one or more protrusions in the cap to engage corresponding protrusions on the outer surface of the LAV to maintain the cap on the LAV after the portion of the LAV is received into the cap.

The above system can, in some implementations, further include one or more of the following features.

The system can further include two or more of the devices attached to a strip of material.

The strip of material can include the removable seal.

The system can further include two or more of the devices connected by the removable seal.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Figure 1:
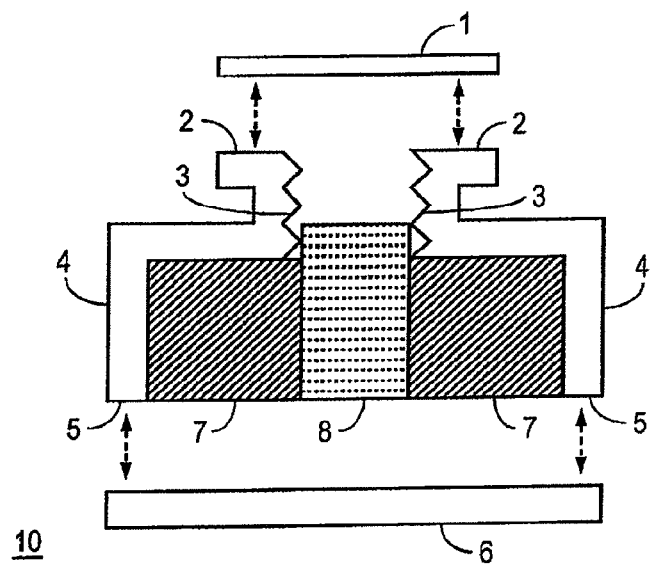
FIG. 1 is a cross-sectional, exploded view of a cleaning device.

In accordance with preferred embodiments, a cleaning device includes a cap having a shape and/or external features to promote easy gripping and a cleaning material in the cap that holds or is in contact with a cleaning agent, such as isopropyl alcohol, for application of the cleaning agent to a site of a medical implement.

The cleaning material can be any substance that can conform, mold or compress in a manner that enables the effective wiping of the site, including the top surface of the site, side surface, and any threads or grooves, if present, and provide the cleaning agent at least at a surface level. Examples of the cleaning material include cotton, open or closed cell foam such as polyethylene foam, or other substance that can hold or carry the cleaning agent. The cleaning agent can be any chemical, substance or material that cleans the site of bacterial or even viral microorganisms, or any carrier that contains such chemical, substance or material. Examples of a cleaning agent include isopropyl alcohol, chlorhexidine, povidone-iodine, hydrogen peroxide, soap, and hydrochloric acid.

The term "medical implement" is used to denote any tool or object that can be used in a medical setting and that can connect to a site cleaning device as described herein according to a number of embodiments. Examples of medical implements include, but are not limited to, access ports on tubing sets (extension sets, T-connectors and IV sets), access ports on catheters (both peripheral and central lines), needle free valves, stopcocks, luer connectors, stethoscopes and other components or devices whereby regular cleaning is desired. Medical implements are commercially available in standard sizes. Thus, the end or opening of a site cleaning device can be provided with fittings to accommodate such standard size medical implements.

The cap of the cleaning device is made of a material that is compatible with the cleaning materials and agents to be used, examples of materials would include, sealed foam, plastic, glass, or metal. The cleaning device may need to undergo sterilization. For securing the cleaning device to another device, the cleaning device can include attachment mechanisms such as "snap-fit" mechanisms or clamps to hold it in place on the other device. Alternatively the cleaning material in the cap may conform to the sides of the medical implement to thereby "grip" and remain secured to the medical implement. The cap also may have threading to secure it in place on a medical implement. The cap may have some cutaway portions on its walls to enable the use of some undercuts during the molding process, and to allow the cleaning material to flex outward both during use. The cap can be made from polyethylene or another material that is stable when in the presence of alcohol or other cleaning agent.

In preferred exemplary embodiments, prior to being applied to a site, and after the cleaning material is provided with a cleaning agent, the opening of the cap is sealed with a foil-based seal or other material suitable for retaining a cleaning agent in the cleaning material and preventing evaporation of the cleaning agent. The cap seal may also be formed in a manner whereby several caps could be attached i.e. a strip, where individual caps can be peeled from the strip in order to be used. These strips of caps can be made conveniently accessible, i.e. hung from intravenous (IV) poles or IV sets, in patient rooms and medication carts, to name just a few. The strips provide the convenience of having several caps available in one location.

The cleaning material in the cap can be an alcohol-soaked piece of gauze, foam or similar cleaning material. The cleaning material can be formed into the general interior shape of the cap from one or more pieces. For instance, the cleaning material can include a ring for circumscriptive coverage and cleaning of the site, and further include a cylinder within the ring for coverage and cleaning on a distal end of the site. A single piece of cleaning material may also be cut or formed to perform the same coverage and cleaning functions as the two pieces described above. The cleaning material may also cover the threads and/or be formed as part of the threads.

In still further embodiments, the cleaning material may be made entirely or partially of the cleaning agent. For example, the cleaning material can be formed of an open cell foam or plastic that is chemically or physically impregnated with a cleaning agent such as povidone or iodine, or isopropyl alcohol.

To further illustrate and describe these concepts, reference is now made to FIG. 1, which shows a cross-sectional, exploded view of a cleaning device, embodied as a cap 10 with a housing 4 that defines an inner cavity 20 of the cap 10. A foil seal 1 is configured to attach to a sealing surface 2 of the housing 4. The housing 4 further includes internal threads 3. In a preferred exemplary embodiment, the internal threads 3 are sized and arranged to accommodate luer threads, i.e. standardized male threads designed to mate with the female threads on a medical implement to which the cap 10 attaches. The housing 4 also has a mating surface 5 for attachment of a bottom portion 6.

Within housing 4 is a first cleaning material 7. The first cleaning material 7 may be attached to the walls of housing 4 by glue, solvent or some other attachment composition or mechanism, or may be held in the housing 4 by compression or trapped between the bottom portion 6 and housing 4. Ribs or protrusions on the inside of the housing 4 may also be used to prevent the cleaning material 7 from slipping or rotating. The first cleaning material 7 is compressible, and is preferably doughnut-shaped or ring-shaped. The first cleaning material 7 is positioned and configured to compress radially in an outwardly direction to scrub or wipe the circumscriptive surface of the site and the surface of the threads of an inserted medical implement.

A second cleaning material 8 is designed to compress in the axial direction upon insertion of the medical implement and is designed to wipe the distal end and distal surface of the inserted medical implement. The second cleaning material 8 may be attached to the walls of bottom portion 6 by glue, solvent or some other attachment composition or mechanism, or affixed to first material 7 by glue, solvent or some other attachment composition or mechanism. Protrusions on the inside of the bottom portion 6 may also be used to prevent the cleaning material 8 from rotating or removal. The first cleaning material 7 and second cleaning material 8 may be formed from a single piece of compressible cleaning material of cotton, foam or other suitable cleaning material adapted for scrubbing. This single piece may be cut completely or partially cut to achieve a similar effect as two separate pieces of cleaning material.

Figure 2:
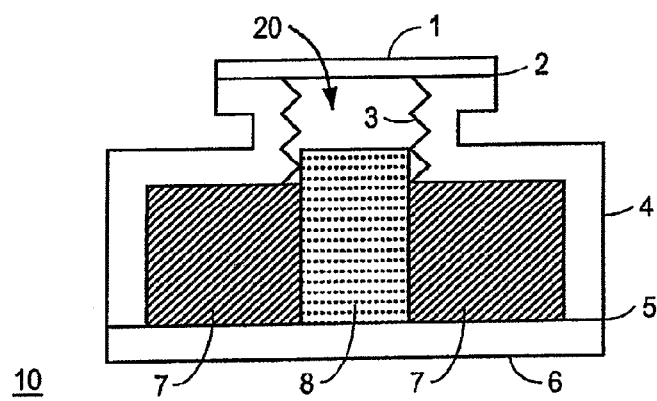
FIG. 2 is a cross-sectional view of an assembled cleaning device.

FIG. 2 illustrates an assembled cap 10. The first and second cleaning materials 7 and 8 in the inner cavity 20 are at least partially saturated with a cleaning agent, such as isopropyl alcohol, or a mix of cleaning agents. The foil seal 1 is then attached to housing 4 at sealing surface 2 by glue, solvent, thermal bonding, etc. A bottom portion 6 is attached to housing 4 at point 5 by glue, welding, solvent, threads or other attachment mechanism or process. With the foil seal 1 and the bottom portion 6 attached to housing 4, the inner cavity 20 is hermetically sealed. The housing 4, bottom portion 6, and first and second cleaning materials 7, 8 are respectively made of a material or cleaning materials that are compatible with the cleaning agent. For instance, if isopropyl alcohol is used for at least part of the cleaning agent, the housing 4 and bottom portion 6 can be constructed of a plastic such as polyethylene. The housing 4 and bottom portion 6 can be formed of a unitary piece of material, as explained further below.

Figure 3:
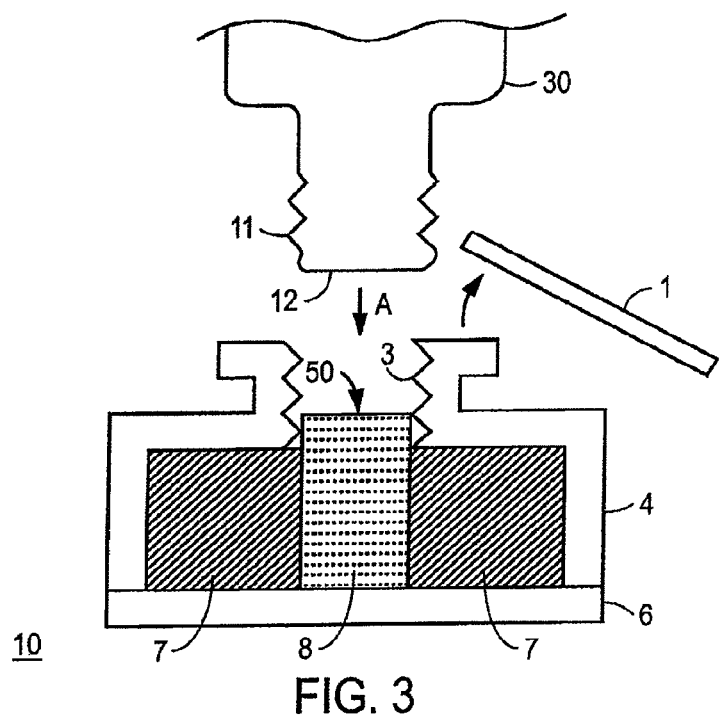
FIG. 3 illustrates operation of a cleaning device for connection to a site of a medical implement.

FIG. 3 illustrates a medical implement 30 moving toward housing 4, in a direction A, which should be recognized as a reference only, and that the housing 4 can likewise be moved toward the medical implement 30. The foil seal 1 is removed from housing 4. In alternative embodiments, the foil seal 1 can be a foil pouch or other sterilized material that would inhibit evaporation of the cleaning agent. A distal end surface 12 of the medical implement 30 is eventually contacted with the upper surface 50 of the second cleaning material 8.

Figure 4:
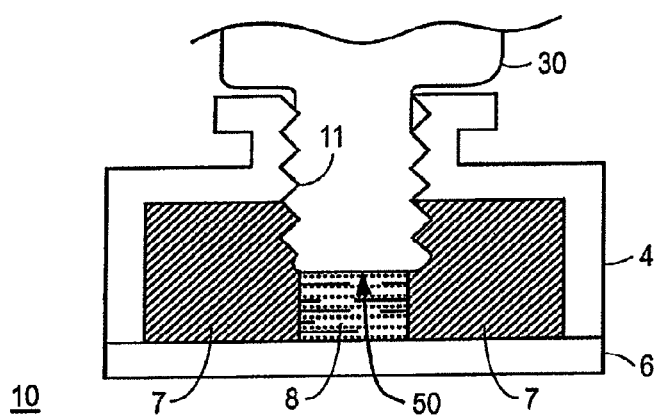
FIG. 4 illustrates a cleaning device connected to a medical implement and cleaning a site of the medical implement.

As the medical implement 30 continues in direction A, it axially compresses second cleaning material 8 continuing to clean surface 12 with surface 50. This movement also begins to radially compress the first cleaning material 7 and to conform the first cleaning material 7 with, and begin scrubbing, threads 11. The cleaning materials 7 and 8 contain the cleaning agent so as to perform a thorough cleaning of the area about the threads 11 and the surface 12. As threads 11 of the medical implement 30 continue to be rotationally inserted into the threads 3 of the housing, the distal end surface 12 is automatically scrubbed by surface 50 of the second cleaning material 8 and cleaned by cleaning agent held therein, and at least a portion of the side and threads 11 of the medical implement 30 are automatically scrubbed by radial compression of the first cleaning material 7 and cleaned by a cleaning agent held therein. FIG. 4 illustrates the disinfecting cap 10 with a fully inserted medical implement 30.

The cap 10 can be removed immediately from the medical implement 30 after use, or be kept in place. If the cap 10 is removed the medical implement 30 surfaces 11 and 12 will be clean and ready for use upon the drying of the cleaning agent. If the cap 10 is kept secured to medical implement 30, the cleaning agent in cap 10 will evaporate over time thereby destroying any microorganisms on the surfaces 12 and 11 of medical implement 30. The cap 10 then maintains the surfaces 11 and 12 of medical implement 30 in a clean and ready-to-access state by eliminating any forms of touch contamination.

Figure 5:
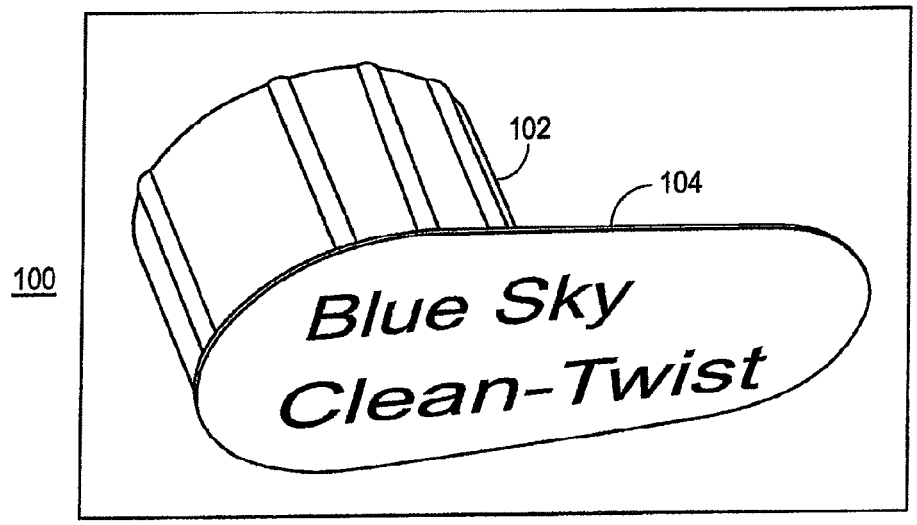
FIG. 5 shows another embodiment of an assembled cleaning device.
Figure 6:
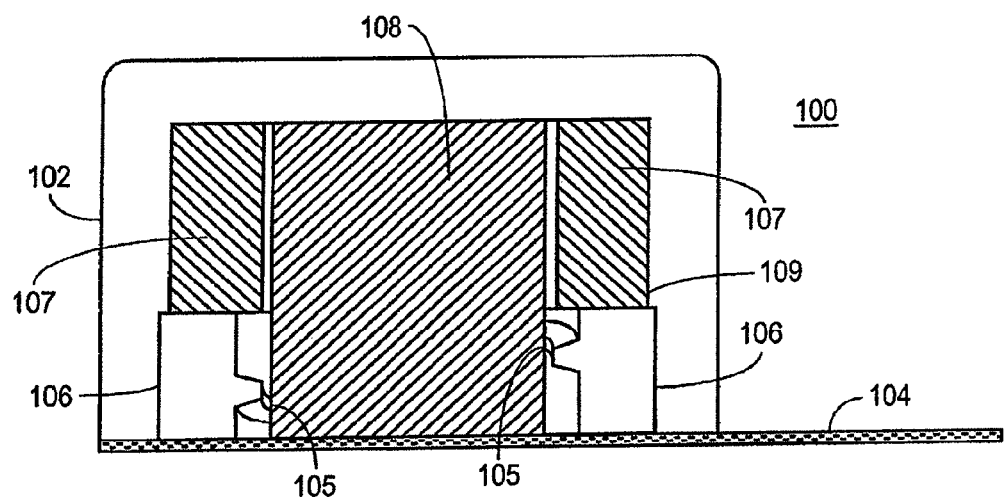
FIG. 6 is a cross-sectional view of an assembled cleaning device in accordance with an embodiment.

FIGS. 5-10 illustrate an alternate embodiment of a cleaning device 100. FIG. 5 is a perspective view of the cleaning device 100 formed of a cap 102 with a seal 104 that is connected to and covers the opening of the cap 102. The cap 102 can have a number of gripping ridges or projecting members for ease of use. FIG. 6 is a cross-sectional view of the cleaning device 100. The cap 102 forms an inner cavity with one opening that is large enough to receive a site of a medical implement. The seal 104 is affixed to the opening and is preferably entirely removable. In other embodiments, the seal 104 is permanently affixed, and is simply punctured by insertion of a site of a medical implement.

The cap 102 houses a threaded ring 106 proximate to the opening. The threaded ring 106 includes one or more threads 105 and is adapted to receive the site of the medical implement to be disinfected, and thus defines the size and shape of the opening. This embodiment is advantageous because it creates a single circumferential seal point, seal 104 to the opening of cap 102.

In some embodiments, the cap 102 and threaded ring 106 are formed of a unitary piece of material or cleaning material. In other embodiments, the threaded ring 106 fits into a groove 109 that is formed in the inside edge surface of the cap 102 near the opening. In this latter configuration, the groove 109 maintains the position of threaded ring 106 near the open end of the cap where the threaded ring top surface may be flush with or slightly recessed from the cap open end walls, and the threaded ring 106 may also include or create with the cap wall a small vent aperture or opening to allow evaporation of a cleaning agent in the cap 102. The threaded ring 106 can be mechanically kept from rotating with internal ribs or protrusions in cap 102 or groove 109. Threaded ring 106 may be held in place within grove 109 and cap 102 by glue, welding, snap-fit, solvent bonding or any other mechanism or composition known to those of requisite skill.

The cleaning device 100 further includes a first cleaning material 107 that holds the cleaning agent, such as isopropyl alcohol, and a second cleaning material 108 that also holds or is at least partially saturated by the cleaning agent. In preferred exemplary embodiments, the first cleaning material 107 is formed as a hollow cylinder or ring positioned between the threaded ring 106 and the top inside surface of the cap 102, and is adapted for radial compression against a site that is inserted into the cap 102 or over which the cap 102 is placed. In some embodiments, the second cleaning material 108 is formed as a solid cylinder and positioned within the hollow space of the first cleaning material 107, and is adapted for axial compression against a leading edge of the site that is inserted into the cap 102 or over which the cap 102 is placed. In other embodiments, cleaning materials 107 and 108 can be made of a single piece of material and cut or formed so as to achieve the same result as described above. The cleaning agent is provided to the cleaning materials 107, 108 prior to the opening being covered with the seal 104.

Figure 7:
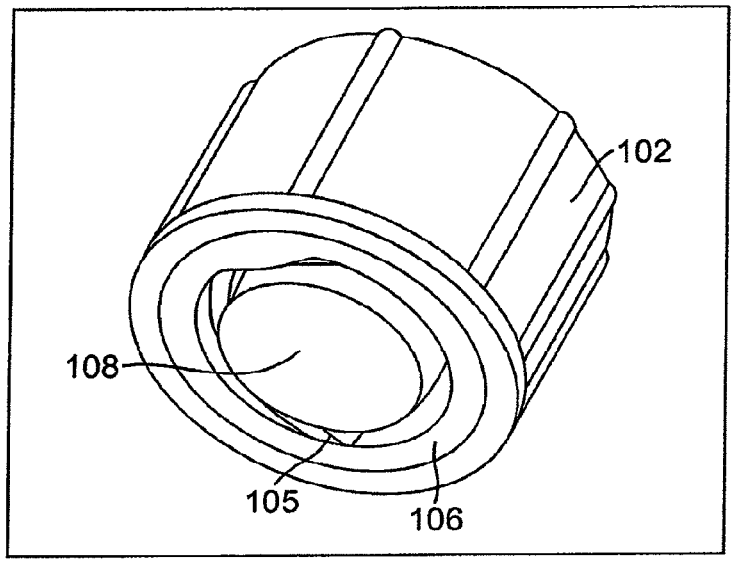
FIG. 7 is a perspective view of another cleaning device.
Figure 8:
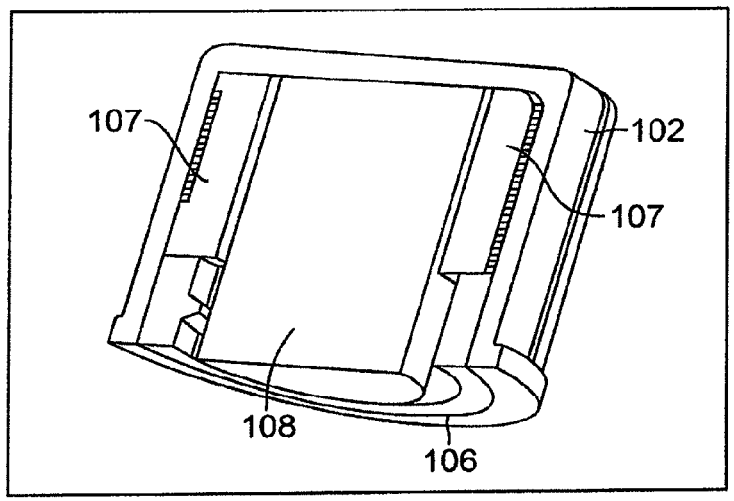
FIG. 8 is a cross section of a cleaning device.
Figure 11:
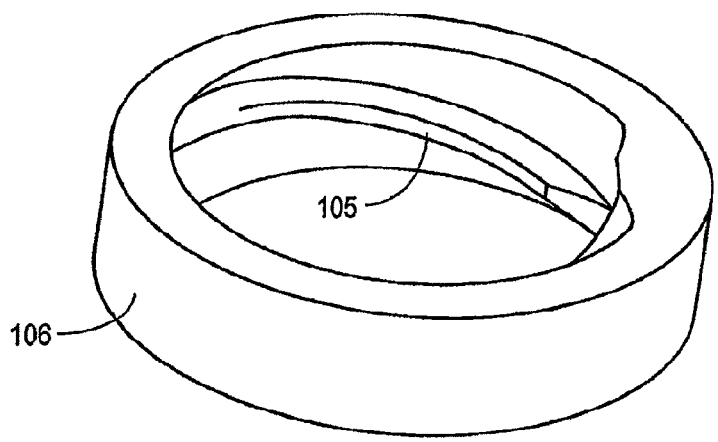
FIG. 11 is a perspective view of a ring that attaches to a corresponding structure of a medical implement.

FIG. 7 is a bottom perspective view and FIG. 8 is a cross-sectional view of the cleaning device 100 with the seal 104 removed, showing the cap 102, threaded ring 106 that sits within the cap 102, and the second cleaning material 108 inside the cap 102. The second cleaning material 108 can extend to and slightly beyond the opening of the cap 102. FIG. 8 further shows the first cleaning material 107 that circumscribes the second cleaning material 108 and being positioned between the threaded ring 106 and the top inner surface of the cap 102. FIG. 11 illustrates an example of the threaded ring 106 and its threads 105. An attribute of this embodiment of the threaded ring 106 shown in FIG. 11 is that there are only two opposing threads that travel 180 degrees before terminating. This enables the molding of threaded ring 106 without the use of a screw to create the thread feature in an injection molding tool. The threaded ring 106 can also be produced with an injection molding tool utilizing a screw.

Figure 9:
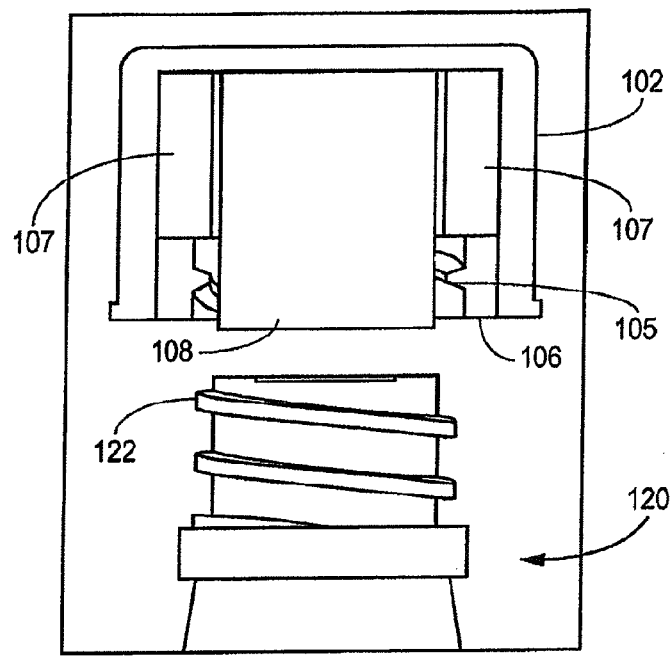
FIGS. 9 and 10 show a cleaning device being used to clean a site of a medical implement.
Figure 10:
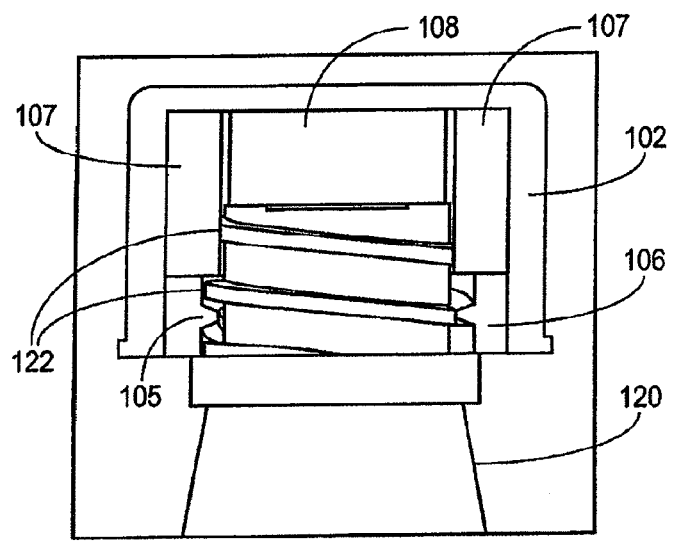

FIG. 9 illustrates the cleaning device 100 about to make contact with a site 120 of a medical implement. As discussed above, the site 120 can be a luer port, a, a needle free valve, an injection port of a vessel, or other medical implement that needs to be cleaned prior to use with a patient. In some embodiments, the site 120 can include a set of threads 122 that correspond to the threads 105 in the threaded ring 106 of the cleaning device 100. The cleaning materials 107 and 108 are preloaded with a cleaning agent, before removal of the seal and contact by the site 120. Accordingly, as shown in FIG. 10, the site 120 makes contact with the cap 102 by a screwing motion relative to the cap 102. The second cleaning material 108 is compressed axially and swabs against the leading edge of the site 120, while the first cleaning material 107 is compressed radially and swabs against sides of the site 120.

FIG. 11 illustrates the molded thread ring 106 with two opposing threads 105 that traverse opposing 180 degree portions of the ring. This design enables the thread ring 106 to be molded without the use of a screw that is typically used to create threaded parts in a molding process. Thus the threaded ring 106 can be manufacture very inexpensively. The threaded ring 106 can also clean some of the threads when the cap is placed into position, and may or may not cover all the threads. In some embodiments, the threaded ring 106 can be molded from the cleaning material, or the cleaning material is formed only of the threaded ring 106. In such embodiments, the cleaning may only occur on threads of the site and in an axial direction.

Figure 12:
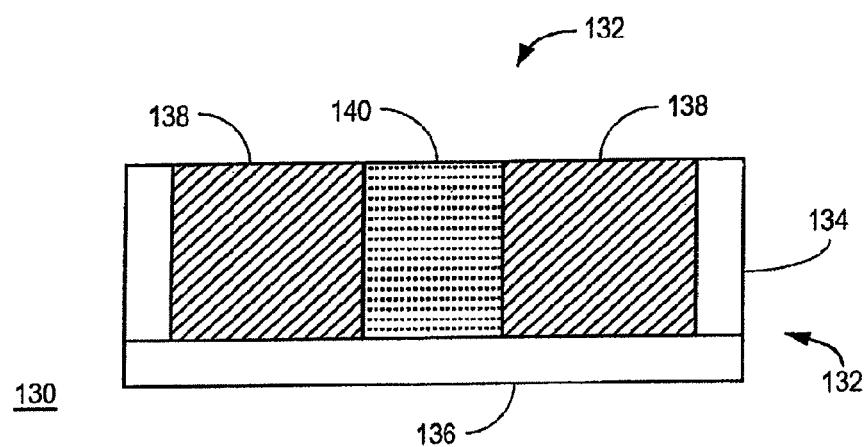
FIG. 12 is a cross sectional view of another alternative embodiment of a cleaning device.

FIG. 12 shows an alternative embodiment of a cleaning device 130 having a cap 132 that is filled with a cleaning material. The cap 132 has side walls 134 and a top 136 that define an inner cavity with an opening 132. The cleaning material includes at least a first cleaning material 138, such as cotton or foam, that delivers a cleaning agent. The cleaning material can include a second cleaning material 140 to hold more cleaning agent. In some embodiments, the second cleaning material 140 can be circumscribed by the first cleaning material 138. Alternatively, the first cleaning material 138 can completely envelope the second cleaning material 140, each providing their own compressibility and capacity to hold a cleaning agent. Still, in other embodiments, the first and second cleaning materials 138, 140 can be formed of a single piece of material. The cleaning material(s) are filled at least partially with a cleaning agent, prior to sealing of the opening 132 with a seal and closure of the inner cavity.

Figure 13:
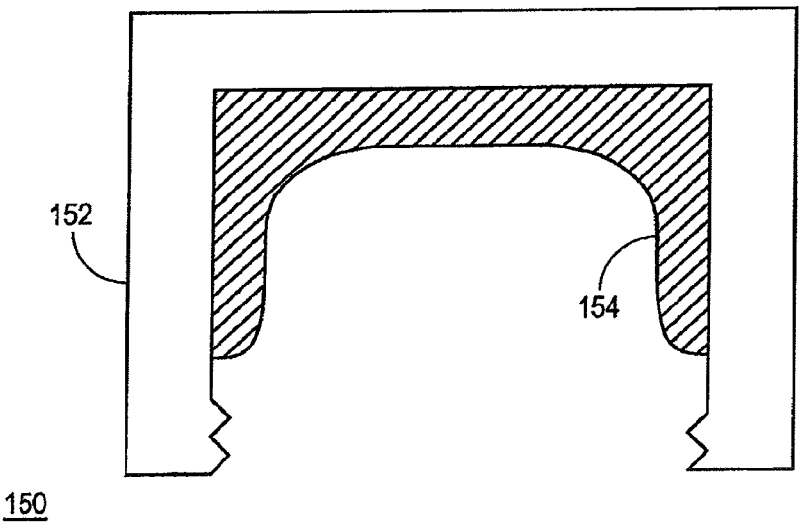
FIG. 13 shows yet another alternative embodiment of a cleaning device.

FIG. 13 shows an alternate embodiment of a cleaning device 150. In this embodiment, the cleaning device 150 includes a housing 152 that is formed as a threaded cap. The inner surface of the housing 152 is covered, at least in part, by a cleaning layer 154 that is bonded to the inner surface of the housing 152. The cleaning layer 154 can be a cleaning material such as cotton, foam, or other porous and pliable material that suitably holds and/or delivers a cleaning agent such as isopropyl alcohol. The cleaning layer 154 is sized and positioned inside the housing 152 so as to be able to swab the top and a portion of the sides of a part of a medical implement that is inserted therein, or over which the housing 152 is placed. Accordingly, the cleaning layer 154 can have any thickness or compressibility.

Figure 14:
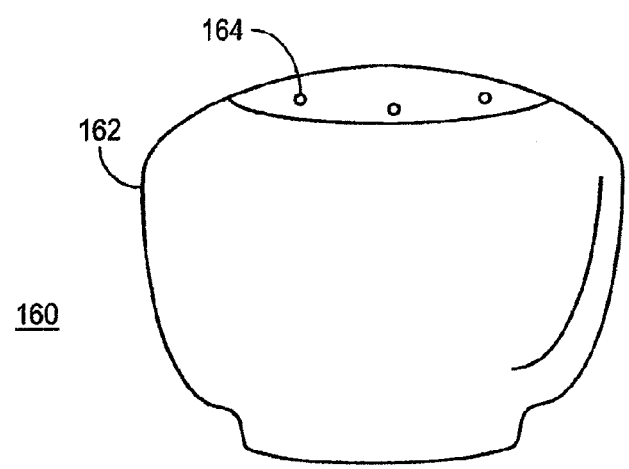
FIG. 14 shows a cap of a cleaning device in accordance with some embodiments.

FIG. 14 shows yet another alternative embodiment of a cleaning device 160, illustrating an outer view of a rounded housing 162 for an expanded inner chamber to hold more cleaning agents or cleaning materials that hold such agents. Holes 164 in the housing 162 can promote evaporation of the cleaning agent, particularly when the housing covers a site of a medical implement to be disinfected. The location of the vent holes is variable and the vent holes can also be sealed with a filter type membrane that permits the drying of the cleaning agents but does not allow entry of microorganisms or fluid.

The use of the various implementations and embodiments above entails the following: the healthcare worker would, with gloved hands, open the foil package and place this cap over the site of a medical implement to be cleaned. Upon placement the alcohol soaked cleaning material wipes all of the port's surfaces. This wipe could be accomplished by either a turning motion (if threads are used) or by simply pushing the cap onto the port. In this way the cap eliminates errors in the practice of swabbing due to poor training or excessive workloads. The cap would then remain secured in place by threads, mechanical tension provided by the foam, cotton, etc., snaps or some other mechanism. A cap in place on a medical implement is a positive indication that a desired site of the medical implement is clean. A vibrant color may be used to allow instant visualization of a cap's presence from a door or hallway. ICP's can review compliance by merely observing sites to see whether or not a cap is in place. The cap could remain in place for periods of up to three days or more. For extended periods the alcohol will likely evaporate, which assures that the site is clean. With the cap in place, it continues to keep the site clean even after the alcohol has evaporated.

Although a few embodiments have been described in detail above, other modifications are possible. For instance, any of the embodiments described above may be sized and scaled for a particular medical implement, such as a stethoscope. Other embodiments may be within the scope of the following claims.

The invention claimed is:

1. A device for cleaning a site of a luer activated valve (LAV), the device comprising:
    a cap having an inner cavity for receiving a site of the LAV, the cap being formed to provide at least one aperture to the inner cavity of the cap when the site of the LAV is received into the inner cavity of the cap;
    one or more protrusions extending inwardly from the cap, the one or more protrusions to engage the site of the LAV to maintain the cap on the site of the LAV after the site of the LAV is received into the inner cavity of the cap;
    a cleaning agent that occupies at least some of the inner cavity, the cleaning agent being formulated to clean the site of the LAV as the inner cavity of the cap receives the site of the LAV and when the cap is maintained on the site of the LAV; and
    a removable seal that seals the cleaning agent within the inner cavity prior to the inner cavity of the cap receiving the site of the LAV.

2. The device in accordance with claim 1, wherein the at least one aperture allows evacuation of at least some of the cleaning agent from the inner cavity when the inner cavity of the cap receives the site of the LAV.

3. The device in accordance with claim 1, wherein the one or more protrusions includes threading.

4. The device in accordance with claim 1, wherein the at least one aperture is formed between the one or more protrusions extending inwardly from the cap and the outer surface of the LAV.

5. The device in accordance with claim 1, wherein the at least one aperture is provided as corresponding protrusions on the site of the LAV engage the one or more protrusions extending inwardly from the cap.

6. The device in accordance with claim 1, further comprising a compressible cleaning material in the inner cavity of the cap to contain a portion of the cleaning agent.

7. A device for cleaning a portion of a luer activated valve (LAV) having an outer surface, the device comprising:
    a cap for receiving the portion of the LAV, the cap being formed to provide at least one aperture to an inner cavity of the cap when the portion of the LAV is received into the cap;
    one or more protrusions to engage the outer surface of the LAV to maintain the cap on the LAV after the portion of the LAV is received into the cap;
    a cleaning agent within the cap to clean the portion of the LAV as the cap is maintained on the LAV; and
    a removable seal that seals the cleaning agent within the cap prior to the cap receiving the portion of the LAV.

8. The device in accordance with claim 7, wherein the at least one aperture allows evacuation of at least some of the cleaning agent from the cap when the cap receives the portion of the LAV.

9. The device in accordance with claim 7, wherein the one or more protrusions includes threading.

10. The device in accordance with claim 7, wherein the at least one aperture is formed between the one or more protrusions of the device and the outer surface of the LAV.

11. The device in accordance with claim 7, wherein the at least one aperture is provided as corresponding protrusions on the portion of the LAV engage the one or more protrusions extending inwardly from the cap.

12. A system for cleaning a portion of a luer activated valve (LAV) having an outer surface that includes one or more protrusions, the system comprising:
    one or more devices, each of the one or more devices comprising:
        a cap having a removable seal that seals a cleaning agent within the cap prior to cleaning the portion of the LAV, the cleaning agent to clean the portion of the LAV, the cap being formed to provide at least one aperture to an inner cavity of the cap after the removable seal is removed and when the portion of the LAV is received into the cap; and
        one or more protrusions in the cap to engage corresponding protrusions on the outer surface of the LAV to maintain the cap on the LAV after the portion of the LAV is received into the cap.

13. The system in accordance with claim 12, further comprising two or more of the devices attached to a strip of material.

14. The system in accordance with claim 13, wherein the strip of material comprises the removable seal.

15. The system in accordance with claim 12, further comprising two or more of the devices connected by the removable seal.

* * * * *